United States Patent
Dutta et al.

(10) Patent No.: US 11,472,925 B2
(45) Date of Patent: Oct. 18, 2022

(54) SILICONE POLYMER

(71) Applicant: Momentive Performance Materials Inc., Waterford, NY (US)

(72) Inventors: Pranabesh Dutta, Bangalore (IN); Vinu Krishnan Appukuttan, Bangalore (IN); Sandeep Naik, Bangalore (IN); Anubhav Saxena, Bangalore (IN)

(73) Assignee: MOMENTIVE PERFORMANCE MATERIALS INC., Waterford, NY (US)

( * ) Notice: Subject to any disclaimer, the term of this patent is extended or adjusted under 35 U.S.C. 154(b) by 0 days.

(21) Appl. No.: 15/928,511

(22) Filed: Mar. 22, 2018

(65) Prior Publication Data

US 2019/0292323 A1    Sep. 26, 2019

(51) Int. Cl.
| | | |
|---|---|---|
| *C08G 77/04* | (2006.01) | |
| *C08G 77/392* | (2006.01) | |
| *A61K 8/899* | (2006.01) | |
| *A61Q 19/00* | (2006.01) | |
| *C08G 77/38* | (2006.01) | |
| *C08G 77/52* | (2006.01) | |
| C08G 77/00 | (2006.01) | |

(52) U.S. Cl.
CPC .......... *C08G 77/392* (2013.01); *A61K 8/899* (2013.01); *A61Q 19/00* (2013.01); *C08G 77/38* (2013.01); *C08G 77/52* (2013.01); *A61K 2800/10* (2013.01); *C08G 77/70* (2013.01); *C08G 77/80* (2013.01)

(58) Field of Classification Search
CPC ......... C08G 77/52; C08G 77/54; C08G 77/48
See application file for complete search history.

(56) References Cited

U.S. PATENT DOCUMENTS

| | | | |
|---|---|---|---|
| 3,395,168 A * | 7/1968 | Piccoli ................. | C07F 7/0838 556/433 |
| 3,398,175 A * | 8/1968 | Leitheiser .............. | C08G 77/52 556/433 |
| 3,668,273 A | 6/1972 | Krantz | |
| 4,226,761 A | 10/1980 | Cooper et al. | |
| 4,513,132 A * | 4/1985 | Shoji .................... | C08G 77/52 524/477 |
| 4,518,758 A * | 5/1985 | Cavezzan .............. | C08G 18/61 525/474 |
| 4,725,658 A | 2/1988 | Thayer et al. | |
| 4,774,028 A | 9/1988 | Imai et al. | |
| 4,814,392 A | 3/1989 | Shea et al. | |
| 5,204,438 A | 4/1993 | Snow et al. | |
| 5,346,980 A * | 9/1994 | Babu .................... | C08G 77/52 528/32 |
| 5,357,022 A | 10/1994 | Banach et al. | |
| 5,380,527 A | 1/1995 | Legrow et al. | |
| 5,596,048 A | 1/1997 | Blohm et al. | |
| 5,916,952 A | 6/1999 | Romenesko et al. | |
| 6,783,692 B2 | 8/2004 | Bhagwagar | |
| 6,815,486 B2 | 11/2004 | Bhagwagar et al. | |
| 6,869,642 B2 | 3/2005 | Freuler et al. | |
| 7,074,490 B2 | 7/2006 | Feng et al. | |
| 7,109,288 B2 | 9/2006 | Akatsuka et al. | |
| 7,256,248 B2 * | 8/2007 | Sugo .................... | C08G 73/125 528/26 |
| 7,579,425 B2 | 8/2009 | Terry et al. | |
| 8,921,507 B2 | 12/2014 | Yoshihara et al. | |
| 9,209,104 B2 | 12/2015 | Nguyen et al. | |
| 2002/0013441 A1 * | 1/2002 | Muller .................. | C08G 77/52 528/10 |
| 2003/0096919 A1 | 5/2003 | Ichinohe | |
| 2007/0051773 A1 | 3/2007 | Ruchert et al. | |
| 2007/0149703 A1 | 6/2007 | Caprasse et al. | |
| 2007/0208144 A1 | 9/2007 | Delsman et al. | |
| 2008/0302064 A1 | 12/2008 | Rauch | |
| 2012/0016083 A1 * | 1/2012 | Kim ....................... | C09J 183/04 525/100 |
| 2012/0046423 A1 * | 2/2012 | Koh ....................... | H01L 23/296 525/478 |

(Continued)

FOREIGN PATENT DOCUMENTS

| | | |
|---|---|---|
| CN | 102634212 | 8/2012 |
| CN | 103849356 | 6/2014 |

(Continued)

OTHER PUBLICATIONS

Shen et al., "Polyethylene nanofibers with very high thermal conductivities." Nature Nanotechnology, 2010, vol. 5 (4), pp. 251-255.
Singh et al., "High thermal conductivity of chain-oriented amorphous polythiophene." Nature Nanotechnology, 2014, vol. 9, pp. 384-390.
Patent Cooperation Treaty (PCT), International Search Report and Written Opinion for Application PCT/US2019/022243 filed Mar. 14, 2019, dated May 29, 2019, International Searching Authority, EP.

(Continued)

*Primary Examiner* — Margaret G Moore

(74) *Attorney, Agent, or Firm* — Joseph Waters; McDonald Hopkins LLC

(57) ABSTRACT

Provided is a polymer of the formula:

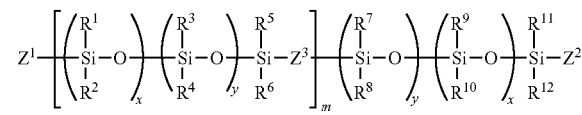

and compositions comprising the same. The polymers comprise a cyclic unsaturated group ($Z^3$) within the siloxane polymer backbone. The polymers have been found to exhibit good thermal conductivity and may find utility in a variety of applications.

9 Claims, No Drawings

(56) References Cited

U.S. PATENT DOCUMENTS

2015/0144987 A1    5/2015  Hamamoto et al.

FOREIGN PATENT DOCUMENTS

| CN | 105018043 | 11/2015 |
| CN | 110770282 A | 2/2020 |
| EP | 0091104 | 10/1983 |
| EP | 0163495 | 12/1985 |
| EP | 2562200 | 2/2013 |
| JP | 11323162 | 11/1999 |
| JP | 2007051221 | 3/2007 |
| JP | 2008214599 | 9/2008 |
| JP | 6125221 | 5/2017 |

OTHER PUBLICATIONS

"Synthesis and Application of Highly Active Catalysts for Hydrosilylation Reactions", Yang Jinsheng et al., Silicon Materials, vol. 20, Issue 1, pp. 26-28.

\* cited by examiner

SILICONE POLYMER

FIELD

The present invention relates to a silicone polymer. In particular, the present invention relates to a functionalized siloxane polymer comprising unsaturated cyclic moieties that exhibits elastomeric properties over a wide range of temperatures.

BACKGROUND

Poly(arylene ether)s are unique engineering thermoplastics materials which have both amorphous and semi-crystalline morphologies led by the complementary chemical links along the polyarylene ether backbone. The ability to display high thermal transitions (or melting points) and stability, fracture and impact toughness, and excellent resistance to oxidation and hydrolysis have enabled them in many commercial application from last many years.

Poly(arylene ether) resins have been blended with polysiloxanes in various forms over the years to develop multiphase materials to expand their applications across multiple industry such as described in U.S. Pat. Nos. 5,916,952 and 4,226,761. These compositions tend to exhibit phase separation and poor flexibility.

As the interest for dimensional stability, low moisture absorption, and high mechanical and dielectric strength continues, the search for well-defined thermoplastic silicone-polyphenylene ether block copolymers continues further. Polymers such as those described in U.S. Pat. Nos. 5,204,438, 3,668,273, and 4,814,392, were developed. Among the poly(arylene ether) resins, poly(arylene ether sulfone) which has recurring or repeating units of one or more diaryl sulfone groups has been one of the most extensively studied thermoplastic in conjunction with polysiloxane in the form of segmented block copolymers. However, these are typically processed by melt processing at elevated temperatures, which limits their applications in certain industries. Other examples of polymers attempting to incorporate poly(arylene ether) moieties are illustrated in U.S. Pat. No. 5,596,048, and U.S. Publication 2007/0208144. Many of these products require sensitive and expensive reagents to produce. Additionally, the products may have undesirably low molecular weight and exhibit poor thermal and hydrolytic stability.

SUMMARY

Provided is an organosiloxane polymer comprising an unsaturated cyclic group. The polymers exhibit reversible thermoplastic behavior. The polymer may be a solid, fluid, gum, or waxy liquid under various conditions. The polymers exhibit enhanced thermal conductivity without incorporating lesser quantity of thermal filler such that the post cure properties of a material formed from the polymer is not significantly affected. Methods of making the modified silicone polymers and methods of making thermally conducting compositions are also disclosed.

In one aspect provided is a polymer of the formula:

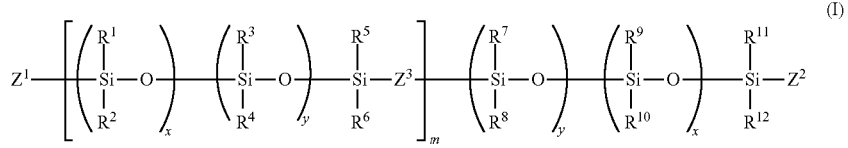

where $R^1$-$R^{12}$ are independently chosen from a hydrogen, a C1-C10 monovalent hydrocarbon group optionally containing a hetero atom, a C6-C20 monovalent aromatic group optionally containing a hetero atom, and a C4 to C30 monovalent saturated or unsaturated cycloalkyl group optionally containing a hetero atom, siloxy group containing 1-20 silicone atoms, $Z^1$ or $Z^2$;

$Z^1$ and $Z^2$ are independently chosen from a hydrogen, C1-C10 hydrocarbon group optionally containing heteroatom, —OH, —NH2, —COOH, or $R^{16}$-A-$R^{17}$— where A is chosen from a group comprising a unsaturated cyclic group chosen from a aromatic group, a functionalized aromatic group, a fused aromatic group optionally containing a heteroatom, a unsaturated alicyclic group, a unsaturated heterocyclic group, or a combination of two or more thereof; $R^{16}$ and $R^{17}$ are independently chosen from a nil, C1-C10 hydrocarbon group optionally containing a hetero atom, a C6-C20 aromatic group optionally containing a hetero atom, and a C4 to C30 saturated or unsaturated cycloalkyl group optionally containing a hetero atom;

$Z^3$ is chosen from —$R^{19}$-A-$R^{19}$— where A is chosen from a group comprising a unsaturated cyclic moiety chosen from an aromatic group, a fused aromatic group, an unsaturated alicyclic group, an unsaturated heterocyclic group, or a combination of two or more thereof, and $R^{19}$ is chosen from a nil, C1-C10 hydrocarbon group optionally containing a hetero atom, a C6-C20 aromatic group optionally containing a hetero atom, and a C4 to C30 saturated or unsaturated cycloalkyl group optionally containing a hetero atom;

m is 1-100; x is 0-200; and y is 0-200, wherein x+y≥1; and (B) (i) a first filler, and (ii) a second filler, where at least one of the first filler and/or the second filler comprises a plurality of filler types differing from one another in terms of particle size and/or morphology.

In one embodiment, A is independently chosen from a C6 to C12 aromatic group; a C10-C36 fused aromatic ring group; a C4-C36 unsaturated alicyclic group; and a C4-C36 unsaturated heterocyclic group.

In one embodiment, A in one or more of Z1, Z2, and Z3 is chosen from a group of the formula -$A^1$-$R^{18}$-$A^2$- where $A^1$ and $A^2$ are independently chosen from a C6 to C12 aryl group, C12-C36 fused aromatic ring group, a C5-C36 unsaturated alicyclic group, and a C5-C36 unsaturated heterocyclic group; and $R^{18}$ is chosen from a direct bond —$(CH_2)_n$—, —$C(CH_3)_2$—, —O—, —S—, —$S(O)_2$—, —C(O)—, C(O)—NH—, —NH—C(O)—NH—, C(O)—O—, —CH=N—, or —CH=N—N=CH— where n is 1-10.

In one embodiment, A is independently chosen from

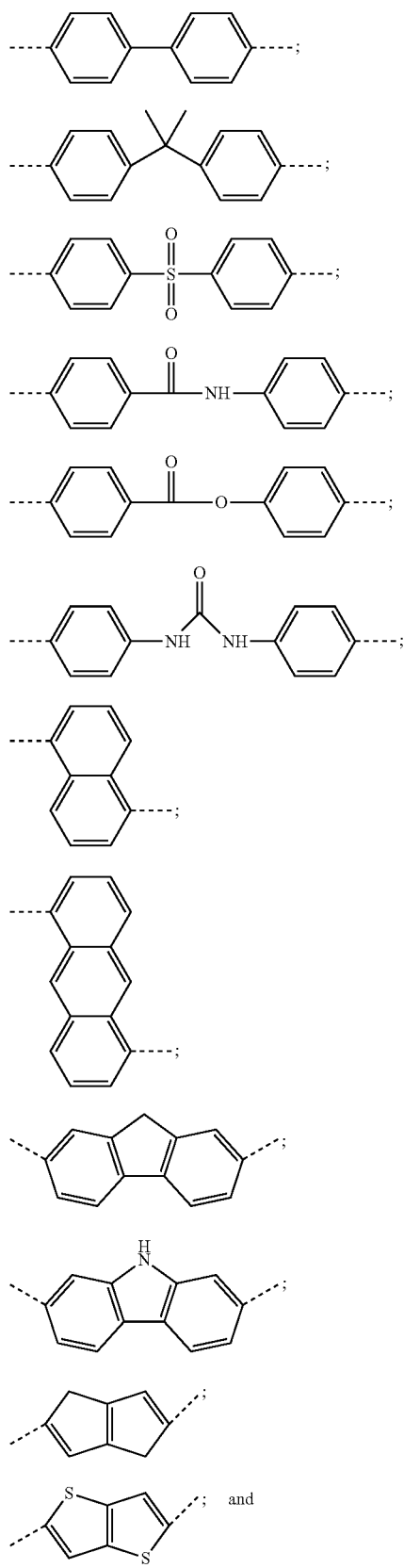

(A-i); (A-ii); (A-iii); (A-iv); (A-v); (A-vi); (A-vii); (A-viii); (A-ix); (A-x); (A-xi); (A-xii); and

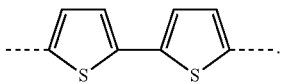

(A-xiii)

In one embodiment, wherein A in $Z^1$, $Z^2$, and $Z^3$ is

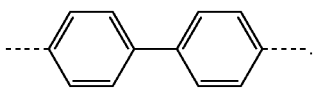

In one embodiment, A in $Z^1$, $Z^2$, and $Z^3$ is

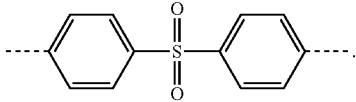

In one embodiment, $R^{16}$ in $Z^1$ and $Z^2$ is chosen from $CH_2=CH_2-(CH_2)_a-$, $CH_2=CH_2-(CH_2)_a-O-$ where a is 0-10; and $R^{17}$ is chosen from a C2-C10 bivalent alkyl group, $-O-(CH_2)_b-$, or $-O-C(O)-(CH_2)_b-$, where b is 2-10; and $R^{19}$ in $Z^3$ is chosen from $R^{17}$.

In one embodiment, the polymer according to any previous embodiment has a number average molecular weight of from about 1000 g/mol to about 50000 g/mol.

In another aspect, provided is an automotive product, household product, paint, coating, laundry detergent, textile treatment, oil or gas product, fuel cell, electronic product, agriculture product, aerospace product, medical or health care product, membrane, construction product, adhesive, sealant, injection moldable and compression moldable rubber or plastic, or silicone based rubber, comprising the polymer of any previous embodiment.

In one embodiment, the product is selected from light emitting devices, computer devices, a stacked die, mobile phones, tablets, flip chip package, hybrid memory cube, touch screens, Wi-Fi device, automotive technology hifi systems, a through-silicon via device, and audio systems, in joints between heat pipes and water tanks in solar heated heating, in fuel cells and wind turbines, in the manufacture of computer chips, gaming consoles, data transfer devices, in light devices, batteries, in housings, coolers, heat exchanging devices, wires, cables, heating wires, refrigerators, dishwashers, air conditionings, accumulators, transformers, lasers, functional clothing, car seats, medical devices, fire protection, electric motors, planes, and trains, as a filament for 3D printing material, drug delivery systems, transdermal patches, wound healing patches, wound dressing patches, patches for scar reduction, transdermal iontophoresis, scaffold for tissue engineering, anti-microbial devices, wound management devices, ophthalmic devices, bioinserts, prostheses, body implants, paints, structural coating, masonry coating, or marine coating, seed coating, superspreader or controlled release fertilizer.

In another aspect, provided is a personal care product comprising the polymer of any previous embodiment.

In one embodiment, the person care product is in the form of an antiperspirant/deodorant, a shaving product, a skin lotion, a moisturizer, a toner, a bath product, a cleansing product, a shampoo, a conditioner, a combined shampoo/conditioners, a mousse, a styling gel, a hair spray, a hair dye, a hair color product, a hair bleach, a waving products, a hair straightener, a nail polish, a nail polish remover, a nail cream or lotions, a cuticle softener, a sunscreen, an insect repellent, an anti-aging product, a lipstick, a foundation, a face powder, an eye liner, an eye shadow, a blush, a makeup, a mascara, a moisturizing preparation, a foundation, a body and hand preparation, a skin care preparation, a face and neck preparation, a tonic, a dressing, a hair grooming aid, an aerosol fixative, a fragrance preparation, an aftershave, a make-up preparation, a soft focus application, a night and day skin care preparation, a non-coloring hair preparation, a tanning preparation, a synthetic and non-synthetic soap bar, a hand liquid, a nose strip, a non-woven application for personal care, a baby lotion, a baby shampoo, a baby conditioner, a shaving preparation, a cucumber slices, a skin pads, a make-up remover, a facial cleansing product, a cold cream, a sunscreen product, a spritzer, a paste mask and mud, a face mask, a cologne and toilet water, a hair cuticle coat, a shower gel, a face and body wash, a personal care rinse-off products, a gel, a foam bath, a scrubbing cleanser, an astringent, a nail conditioner, an eye shadow stick, a powder for face or eye, a lip balm, a lip gloss, a hair care pump spray, a hair-frizz-control gel, a hair leave-in conditioner, a hair pomade, a hair de-tangling product, a hair fixative, a hair bleach product, a skin lotion, a pre-shave and pre-electric shave, an anhydrous cream and lotion, an oil/water emulsion, a water/oil emulsion, a water-resistant cream or lotion, an anti-acne preparation, a mouth-wash, a massage oil, a toothpaste, a clear gel or stick, an ointment base, a topical wound-healing product, an aerosol talc, a barrier spray, a vitamin and anti-aging preparation, an herbal-extract preparation, a bath salt, a bath and body milk, a hair styling aid, a hair-, eye-, nail- and skin-soft solid application, a controlled-release personal care product, a hair conditioning mist, a skin care moisturizing mist, a skin wipe, a pore skin wipe, a pore cleaner, a blemish reducer, a skin exfoliator, a skin desquamation enhancer, a skin towelette or cloth, a depilatory preparation, or a personal care lubricant.

DETAILED DESCRIPTION

Reference will now be made to exemplary embodiments, examples of which are illustrated in the accompanying drawings. It is to be understood that other embodiments may be utilized and structural and functional changes may be made. Moreover, features of the various embodiments may be combined or altered. As such, the following description is presented by way of illustration only and should not limit in any way the various alternatives and modifications that may be made to the illustrated embodiments. In this disclosure, numerous specific details provide a thorough understanding of the subject disclosure. It should be understood that aspects of this disclosure may be practiced with other embodiments not necessarily including all aspects described herein, etc.

As used herein, the words "example" and "exemplary" mean an instance, or illustration. The words "example" or "exemplary" do not indicate a key or preferred aspect or embodiment. The word "or" is intended to be inclusive rather than exclusive, unless context suggests otherwise. As an example, the phrase "A employs B or C," includes any inclusive permutation (e.g., A employs B; A employs C; or A employs both B and C). As another matter, the articles "a" and "an" are generally intended to mean "one or more" unless context suggest otherwise.

Provided is a functionalized silicone polymer and compositions comprising the same. In particular, provided is a functionalized siloxane polymer. The functionalized siloxane polymer is a (AB)n-type siloxane polymer comprising organic groups within the siloxane chain. The siloxane polymer comprises organic groups comprising unsaturated cyclic moieties.

Provided is a silicone polymer having the formula:

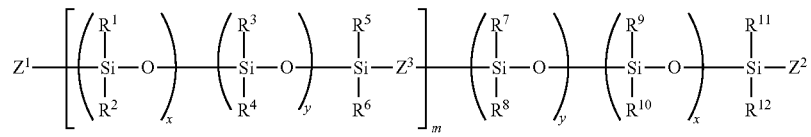

where $R^1$-$R^{12}$ are independently chosen from a hydrogen, a C1-C10 monovalent hydrocarbon group optionally containing a hetero atom, a C6-C20 monovalent aromatic group optionally containing a hetero atom, and a C4 to C30 monovalent saturated or unsaturated cycloalkyl group optionally containing a hetero atom, siloxy group containing 1-20 silicone atoms, $Z^1$ or $Z^2$; $Z^1$ and $Z^2$ are independently chosen from a hydrogen, C1-C10 hydrocarbon group optionally containing heteroatom, —OH, —NH2, —COOH, or $R^{16}$-A-$R^{17}$— where A is chosen from a group comprising a unsaturated cyclic group chosen from a aromatic group, a fused aromatic group, a unsaturated alicyclic group, a unsaturated heterocyclic group, or a combination of two or more thereof; $R^{16}$ and $R^{17}$ are independently chosen from a nil, C1-C10 hydrocarbon group optionally containing a hetero atom, a C6-C20 aromatic group optionally containing a hetero atom, and a C4 to C30 saturated or unsaturated cycloalkyl group optionally containing a hetero atom; $Z^3$ is chosen from —$R^{19}$-A-$R^{19}$— where A is chosen from a group comprising a unsaturated cyclic moiety chosen from an aromatic group, a fused aromatic group, an unsaturated alicyclic group, an unsaturated heterocyclic group, or a combination of two or more thereof; and $R^{19}$ is chosen from a nil, C1-C10 hydrocarbon group optionally containing a hetero atom, a C6-C20 aromatic group optionally containing a hetero atom, and a C4 to C30 saturated or unsaturated cycloalkyl group optionally containing a hetero atom; m is 1-100; x is 0-200; and y is 0-200.

As used herein, an unsaturated alicyclic group refers to an aliphatic cyclic group comprising one or more unsaturated bonds. In embodiments, the unsaturated alicyclic group comprises at least one C=C bond. In embodiments, the unsaturated alicyclic group is chosen from a C4-C36 alicyclic group comprising one or more C=C bonds. The unsaturated alicyclic group may comprise a single ring, a fused ring system, or a bicyclic ring system. Non-limiting examples of unsaturated alicyclic compounds include, but are not limited to, cyclopentene, cyclohexene, cyclopentadiene, dicyclopentadiene, etc.

As used herein, an unsaturated heterocyclic group refers to a cyclic group comprising at least one unsaturated bond and at least one heteroatom within the ring structure. The unsaturated group may be a C=C or an unsaturated bond between a carbon atom and a heteroatom.

In embodiments, the siloxane polymer comprises a curable functional group. In such embodiments, the siloxane comprises at least one $Z^1$ or $Z^2$ group with a curable functional group such as an allyl, vinyl, allyloxy, vinyloxy, acrylate, methacrylate, etc. In one embodiment, $R^{16}$ in the $Z^1$ or $Z^2$ group is chosen from $CH_2=CH_2-(CH_2)_a-$, $CH_2=CH_2-(CH_2)_a-O-$, $CH_2=CH_2-(CH_2)_a-C(O)-O-$, where a is 0-10. In one embodiment, $R^{16}$ is $CH_2=CH_2-(CH_2)_a-O-$ where a is 0. In one embodiment, $R^{16}$ is $CH_2=CH_2-(CH_2)_a-O-$ where a is 1.

$R^{17}$ in $Z^1$ and $Z^2$ (and $R^{19}$ in $Z^3$) is chosen from a $C_2$-$C_{10}$ divalent alkyl group, $-O-(CH_2)_b-$, or $-O-C(O)-(CH_2)_b-$, where b is 2-10.

In embodiments, A in $Z^1$, $Z^2$, and $Z^3$ are independently chosen from a C6 to C12 aryl group, a C10 to C36 fused aromatic group, a C4-C36 unsaturated alicyclic group, and a C4-C36 unsaturated heterocyclic group.

In one embodiment, A for one or more of $Z^1$, $Z^2$, or $Z^3$ is chosen from a group of the formula -$A^1$-$R^{18}$-$A^2$- where $A^1$ and $A^2$ are independently chosen from a C6 to C12 aryl group, a C12-C36 fused aromatic ring, a C5-C36 unsaturated alicyclic group, and a C5-C36 unsaturated heterocyclic group; and $R^{18}$ is chosen from a direct bond, $-(CH_2)_n-$, $-C(CH_3)_2-$, $-O-$, $-S-$, $-S(O)_2-$, $-C(O)-$, $C(O)-NH-$, $-NH-C(O)-NH-$, $C(O)-O-$, $-CH=N-$, or $-CH=N-N=CH-$ where n is 1-10. In embodiments, n is 1-6, 1-4, or 1-2.

Examples of suitable groups for the A groups include, but are not limited to:

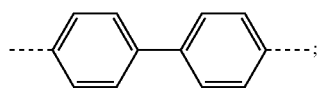
(A-i)

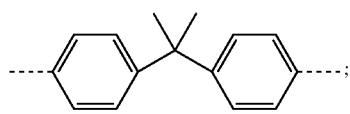
(A-ii)

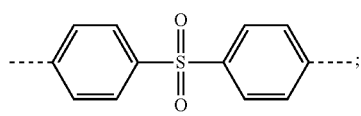
(A-iii)

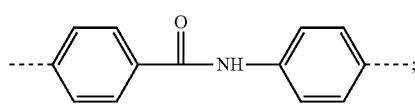
(A-iv)

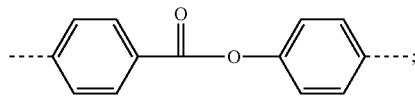
(A-v)

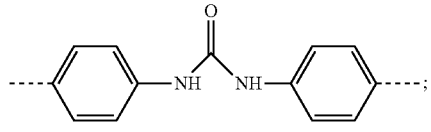
(A-vi)

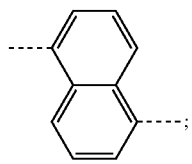
(A-vii)

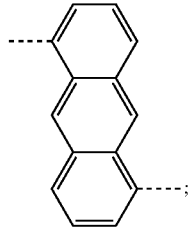
(A-viii)

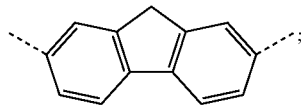
(A-ix)

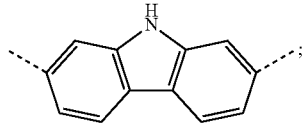
(A-x)

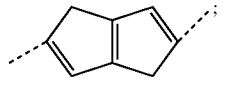
(A-xi)

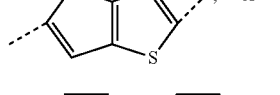
(A-xii)

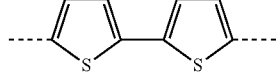
(A-xiii)

Examples of suitable $Z^3$ groups include, but are not limited to, a benzenediyl group, a naphthalenediyl group, a biphenyldiyl group, an acenaphthylene-5,6-diyl group, a pyridine-2,3-diyl group, a pyridine-2,6-diyl group, a H-imidazole-4,5-diyl group, a 1H-pyrrole-2,4-diyl group, a furan-2,5-diyl group and a thiophene-2,5-diyl group. Examples of the benzidyl group include a 1,2-benzenediyl group, a 1,3-benzenediyl group, and a 1,4-benzenediyl group. Examples of the naphthalenediyl group include a 1,2-naphthalenediyl group, a 1,3-naphthalenediyl group, a 1,4-naphthalenediyl group, a 1,5-naphthalenediyl group, a 1,6-naphthalenediyl group, a 1,7-naphthalenediyl group, a 1,8-naphthalenediyl group, a 2,3-naphthalenediyl group, a 2,6-naphthalenediyl group, and a 2,7-naphthalenediyl group. Examples of the biphenyldiyl group include a biphenyl-4,4'-diyl group.

Examples of the biphenyldiyl group include a 4,4'-biphenyldiyl group, a 3,3'-biphenyldiyl group, a 4,4'-(2,2'-diphenylpropane)diyl group, a 3,3'-(2,2'-diphenylpropane)diyl group, a 4,4'-(diphenylsulfone)diyl group, a 3,3'-(diphenylsulfone)diyl group, a 4,4'-(3,3-diphenylhexafluoropropane)diyl group, a 3,3'-(3,3-diphenylhexafluoropropane)diyl group, a 4,4'-(diphenyl ether)diyl group, a 3,3'-(diphenyl ether)diyl group, a 4,4'-(diphenylketone)diyl group, a 3,3'-(diphenylketone)diyl group, a 4,4'-(2,2'-dimethylbiphenyl)

diyl group, a 4,4'-(2,2'-bis(trifluoromethy)biphenyl)biphenyl)diyl group and a 4,4'-(2,6,2',6'-tetramethylbiphenyl)diyl group.

In one embodiment, $R^1$-$R^{12}$ are a C1-C4 alkyl, A in $Z^1$, $Z^2$, and $Z^3$ is

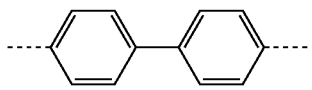

$R^{16}$ in $Z^1$ and $Z^2$ is chosen from $CH_2=CH_2-(CH_2)_a-$, $CH_2=CH_2-(CH_2)_a-O-$ where a is 0-10; and $R^{17}$ is chosen from a C2-C10 bivalent alkyl group, $-O-(CH_2)_b-$, or $-O-C(O)-(CH2)_b-$, where b is 2-10; and $R^{19}$ in $Z^3$ is chosen from $R^{17}$. In one embodiment, $R^{16}$ is $CH_2=CH_2-(CH_2)_a-O-$ where a is 0. In one embodiment, $R^{16}$ is $CH_2=CH_2-(CH_2)_a-O-$ where a is 1.

In one embodiment, $R^1$-$R^{12}$ are a C1-C4 alkyl, A in $Z^1$, $Z^2$, and $Z^3$ is

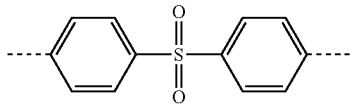

$R^{16}$ in $Z^1$ and $Z^2$ is chosen from $CH_2=CH_2-(CH_2)_a-$, or $CH_2=CH_2-(CH_2)_a-O-$ where a is 0-10; and $R^{17}$ is chosen from a C2-C10 bivalent alkyl group, $-O-(CH_2)_b-$, or $-O-C(O)-(CH_2)_b-$, where b is 2-10; and $R^{19}$ in $Z^3$ is chosen from $R^{17}$. In one embodiment, $R^{16}$ is $CH_2=CH_2-(CH_2)_a-O-$ where a is 0. In one embodiment, $R^{16}$ is $CH_2=CH_2-(CH_2)_a-O-$ where a is 1.

In one embodiment, A is chosen from any one of (A-i)-(A-xiii), and $R^{16}$ in $Z^1$ and $Z^2$ is chosen from $CH_2=CH_2-(CH_2)_a-$, $CH_2=CH_2-(CH_2)_a-O-$ where a is 0-10; and $R^{17}$ is chosen from a C2-C10 bivalent alkyl group, $-O-(CH_2)_b-$, or $-O-C(O)-(CH_2)_b-$, where b is 2-10; and $R^{19}$ in $Z^3$ is chosen from $R^{17}$. In one embodiment A is chosen from any of (A-i)-(A-xiii); $R^{16}$ is chosen from $CH_2=CH_2-(CH_2)_a-O-$ where a is 0 and $R^{17}$ is chosen from $-O-(CH_2)_b-$ where b is 2. In one embodiment A is chosen from any of (A-i)-(A-xiii); $R^{16}$ is chosen from $CH_2=CH_2-(CH_2)_a-O-$ where a is 0 and $R^{17}$ is chosen from $-O-(CH_2)_b-$ where b is 3. In one embodiment A is chosen from any of (A-i)-(A-xiii); $R^{16}$ is chosen from $CH_2=CH_2-(CH_2)_a-O-$ where a is 1 and $R^{17}$ is chosen from $-O-(CH_2)_b-$ where b is 2. In one embodiment A is chosen from any of (A-i)-(A-xiii); $R^{16}$ is chosen from $CH_2=CH_2-(CH_2)_a-O-$ where a is 1 and $R^{17}$ is chosen from $-O-(CH_2)_b-$ where b is 3.

In one embodiment, the polymer may have a formula as described with respect to any of the preceding embodiments, where any of the following may apply separately or in combination with one another:
  m is 1-100; m is 5-90; m is 10-80; m is 20-75; m is 30-60; or m is 40-50;
  x is 0-200; x is 10-175; x is 25-150; x is 50-150; x is 75-125; x is 80-100;
  y is 0-200; y is 10-175; y is 25-150; y is 50-150; y is 75-125; y is 80-100.
It will be appreciated that numerical values can be combined to form new and non-specified ranges.

The present polymers may be formed via hydrosilylation of an appropriate unsaturated compound and a silyl hydride in the presence of a catalyst. The unsaturated compounds to provide the $Z^1$-$Z^3$ groups may be of the formula $R^{16}$-A-$R^{16'}$ where A is as described above, and $R^{16}$ and $R^{16'}$ are independently chosen from allyl, vinyl, allyloxy, vinyloxy, acrylate, or methacrylate. In embodiments, $R^{16}$ and $R^{16'}$ are independently chosen from $CH_2=CH_2-(CH_2)_a-$, $CH_2=CH_2-(CH_2)_a-O-$, $CH_2=CH_2-(CH_2)_a-C(O)-O-$, where a is 0-10. The silyl hydride may be, for example, a siloxane with terminal silyl hydride functional groups or with a Si—H containing group within the main chain of the siloxane.

Useful catalysts include those compounds or molecules that can catalyze the hysrosilylation reaction between a reactive SiH-containing moiety or substituent and a carbon-carbon bond such as a carbon-carbon double bond. Also, in one or more embodiments, these catalysts may be soluble within the reaction medium. Types of catalysts include transition metal compounds including those compounds that include a Group VIII metal. Exemplary Group VIII metals include palladium, rhodium, germanium, and platinum. Exemplary catalyst compounds include chloroplatinic acid, elemental platinum, chloroplatinic acid hexahydrate, complexes of chloroplatinic acid with sym-divinyltetramethyldisiloxane, dichloro-bis(triphenylphosphine) platinum (II), cis-dichloro-bis(acetonitrile) platinum (II), dicarbonyldichloroplatinum (II), platinum chloride, and platinum oxide, zero valent platinum metal complexes such as Karstedt's catalyst, [Cp*Ru(MeCN)$_3$]PF$_6$, [PtCl$_2$(cyclooctadiene)], solid platinum supported on a carrier (such as alumina, silica or carbon black), platinum-vinylsiloxane complexes (e.g., Pt$_n$(ViMe$_2$SiOSiMe$_2$Vi), and Pt[(MeViSiO)$_4$]d)), platinum-phosphine complexes (e.g., Pt(PPh$_3$)$_4$ and Pt(PBU$_3$)$_4$)), and platinum-phosphite complexes (e.g., Pt[P(Oph)$_3$]$_4$ and Pt[P(Obu)$_3$]$_4$)), wherein Me represents methyl, Bu represents butyl, "Vi" represents vinyl and Ph represents phenyl, and c and d represent integers. Others include RhCl(PPh$_3$)$_3$, RhCl$_3$, Rh/Al$_2$O$_3$, RuCl$_3$, IrCl$_3$, FeCl$_3$, AiCl$_3$, PdCl$_2$.2H$_2$O, NiCl$_2$, TiCl$_4$, etc.

In one embodiment, the silicone polymer has a number average molecular weight of from about 1000 g/mol to about 50000 g/mol; from about 2000 g/mol to about 40000 g/mol; even from about 3000 g/mol to about 10000 g/mol. Molecular weight may be determined by GPC, light scattering.

The polymers exhibit properties that make them useful in a variety of applications. The properties or state of the polymer can be controlled or tuned by controlling various aspects of the polymer. In particular, the polymer may be provided as a liquid, a gum, or a solid by controlling the degree of polymerization, silicone chain length, and molecular weight.

The present polymers have been found to exhibit desirable properties that may make them suitable for a wide variety of applications. The polymers have high thermal stability, refractive index, and thermal conductivity.

In one aspect, the polymers may be provided as a composite with a thermally conductive filler. The polymers exhibit excellent wetting behavior when combined with inorganic fillers such that the fillers are readily dispersed in the polymer. These properties allow for providing a material with excellent thermal conductivity. Such materials may be used in products for a variety of applications including, for example, automotive, electronic, construction, aerospace, aviation, medical, personal care, etc. The polymers including as a composite with the thermally conductive filler may be employed as a thermal interface material.

Examples of suitable thermally conductive fillers include, but are not limited to, boron nitride, silica, glass fibers, a metal oxide such as, zinc oxide, magnesium oxide, beryllium oxide, titanium oxide, zirconium oxide, yttrium oxide, etc., calcium carbonate, talc, mica, wollastonite, clays, exfoliated clays, alumina, aluminum nitride, graphite, metallic powders, e.g., aluminum, copper, bronze, brass, etc., or a combination of two or more thereof.

The particle size of the filler materials may be chosen as desired for a particular purpose or intended application. In embodiments, the filler material has an average particle size of from about 0.01 μm to about 500 μm; from about 0.1 to about 250 μm; from about 1 to about 100 μm; from about 5 to about 75 μm; even from about 10 to about 50 μm. It will be appreciated that the composition may comprise a combination of inorganic fillers of different average particle sizes. Such combinations may be chosen as desired for a particular purpose or intended application. In one embodiment, the composition comprises a first organic filler having an average particle size from about 0.01 to about 0.1 μm; a second filler having an average particle size of about 1 μm to about 25 μm; and optionally a third filler having an average particle size of about 50 μm to about 100 μm. The first, second, and third fillers may be the same or different from one another in terms of the chemical makeup of the filler.

The silicone polymer may be blended with a silicone fluid to form a physical gel. As used herein, a "physical gel" refers to a material comprising a compound capable of being arranged in the form of a finely dispersed solid phase in a predominant liquid phase and of forming a network of low density which is easy to destructure by virtue of the presence of weak bonds, this network being reversible.

The silicone fluid can be selected from among any suitable silicone fluid For example, the silicone fluid that can be an organopolysiloxane, a silicone copolyol, a disiloxane, trisiloxane, tetrasiloxane, a trimethicone, an alkylsiloxane or a cyclopolysiloxane, or combinations thereof.

Examples of suitable silicone fluids include branched, unbranched, linear, or cyclic silicone fluids such as those having a viscosity≤8 centistokes, and having, for example from 2 to 7 silicon atoms, these silicones optionally comprising alkyl, polyether- or alkoxy groups having from 1 to 12 carbon atoms. Some non-limiting examples of suitable silicone fluids include octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane, capryl methicone, PEG/PPG 5/3 Methicone, and mixtures of two or more thereof.

Other suitable silicone fluids include, for example, polydimethylsiloxanes (PDMS), polydimethylsiloxanes comprising alkyl, polyether- or alkoxy groups, pendant and/or at the silicone chain end, the alkyl and alkoxy groups each having from 1 to 12 carbon atoms, phenylated silicones such as ethylmethicone, heptylmethicone, hexylmethicone, propylmethicone, isopropylmethicone, heptylmethicone, sec-butylmethicone, tert-butylmethicone, pentylmethicone, phenyltrimethicones, phenyldimethicones, phenyltrimethylsiloxydiphenylsiloxanes, diphenyldimethicones, diphenylmethyl-diphenyltrisiloxanes and (2-phenylethyl)trimethylsiloxy-silicates.

Some non-limiting examples of trisiloxanes suitable as the silicone fluid include linear alkyltrisiloxanes. An example of an alkyltrisiloxane is ethyltrisiloxane, octyltrisiloxane, hexyltrisiloxane, etc. Some specific trisiloxanes include 1,1,1,3,5,5,5-heptamethyl-3-ethyltrisiloxane; 1,1,1,3,5,5,5-heptamethyl-3-octyltrisiloxane; 1,1,1,3,5,5,5-heptamethyl-3-hexyltrisiloxane, and combinations of two or more thereof. In one specific embodiment herein the trisiloxane can be a trisiloxane such as those described in U.S. Patent Application Publication No. 2004/0197284A1 or U.S. Patent Application Publication No. 2005/0069564A1, the contents of each of which are incorporated by reference herein in its entirety. Still more specific examples of trisiloxane include 3-pentyl-1,1,1,3,5,5,5-heptamethyltrisiloxane; 1,1,1,3,5,5,5-heptamethyl-3-octyltrisiloxane, sold, for example, under the name "Silsoft 034" by Momentive Performance Materials Inc.; 1,1,1,3,5,5,5-heptamethyl-3-hexyltrisiloxane; 3-(1-ethylbutyl)-1,1,1,3,5,5,5-heptamethyltrisiloxane; 1,1,1,3,5,5,5-heptamethyl-3-(1-methylpentyl)trisiloxane; 1,1,1,3,5,5,5-heptamethyl-3-(1-methylpropyl)trisiloxane; 3-(1,1-dimethylethyl)-1,1,1,3,5,5,5-heptamethyltrisiloxane; 1,1,1,5,5,5-hexamethyl-3,3-bis(1-methylethyl)trisiloxane; 3-(3,3-dimethylbutyl)-1,1,1,3,5,5,5-heptamethyltrisiloxane; 1,1,1,3,5,5,5-heptamethyl-3-(3-methylbutyl)trisiloxane; 1,1,1,3,5,5,5-heptamethyl-3-(3-methylpentyl)trisiloxane; 1,1,1,3,5,5,5-heptamethyl-3-(2-methylpropyl)trisiloxane; 1,1,1,3,5,5,5-heptamethyl-3-propyltrisiloxane; 3-isohexyl-1,1,1,3,5,5,5-heptamethyltrisiloxane; 3-tert-pentyl-1,1,1,3,5,5,5-heptamethyltrisiloxane; 3-neo-pentyl-1,1,1,3,5,5,5-heptamethyltrisiloxane; 1,1,1,5,5,5-hexamethyl-3,3-dipropyltrisiloxane; 3,3-diethyl-1,1,1,5,5,5-hexamethyltrisiloxane; 3,3-dibutyl-1,1,1,5,5,5-hexamethyltrisiloxane; 3-ethyl-1,1,1,3,5,5,5-heptamethyltrisiloxane; 3-heptyl-1,1,1,3,5,5,5-heptamethyltrisiloxane; 1,1,1,5,5,5-hexamethyl-3,3-diethyltrisiloxane; 1,1,1,3,5,5,5-heptamethyl-3-butyltrisiloxane, and combinations of two or more thereof.

Additionally, other commercially available polysiloxanes include, but are not limited to, Toray FZ-3196 from Dow Corning Inc., SilCare Silicone 41M15 from Clariant Inc., Sibrid AM 108 from Gelest, or combinations thereof. Also, mixtures such as, but not limited to, Hydrobrite 2000 Gel (from Chemtura formerly Witco) or SilCare 51M15 Trimethylsiloxysilicate in Caprylylmethicone (from Clariant) are suitable polysiloxanes for the silicone fluid.

In embodiments, the copolymer of the present invention may also find use as a thixotropic agent or a rheology modifying agent. A "thixotropic agent" as used herein is one that increases the thixotropy of the composition in which it is contained, promoting shear thinning and enabling use of reduced injection force.

The present polymers may be curable or non-curable. Curable polymers will generally comprise a curable functional group attached to the polymer. The curable polymers may be cured by either condensation curing mechanisms or thermal curing mechanisms. In one embodiment, the polymers are condensation curable. Any suitable components may be employed to promote condensation curing such as a condensation catalyst that promotes the condensation of completely or partially hydrolyzed topcoat material. The catalyst can be a catalyst suitable for promoting the curing of siloxanes. Advantageously, condensation catalysts can be employed. Suitable condensation catalysts include, but are not limited to, dialkyltin dicarboxylates such as dibutyltin dilaurate and dioctyltin dilaurate, tertiary amines, the stannous salts of carboxylic acids, such as stannous octoate and stannous acetate, etc. Other useful catalysts include zirconium-containing, aluminum-containing, and bismuth-containing complexes such as K-KAT® XC6212, K-KAT® 5218 and K-KAT® 348, supplied by King Industries, Inc., titanium chelates such as the TYZOR® types, available from DuPont company, and the KR types, available from Kenrich Petrochemical, Inc., and other organometallic catalysts, e.g., those containing a metal such as Al, Zn, Co, Ni, Fe, etc.

In one embodiment, the polymers are thermal curable and comprise a thermal cure catalyst. In one embodiment, the thermal cure catalyst is chosen from an alkyl ammonium carboxylate. The alkyl ammonium carboxylate may be a di-, tri-, or tetra-ammonium carboxylate. In one embodiment, the catalyst is chosen from a tetrabutylammonium carboxylate of the formula: $[(C_4H_9)_4N]^+[OC(O)-R]^-$, wherein R is selected from the group consisting of hydrogen, alkyl groups containing about 1 to about 8 carbon atoms, and aromatic groups containing about 6 to 20 carbon atoms. In embodiments, R is a group containing about 1 to 4 carbon atoms, such as methyl, ethyl, propyl, butyl, and isobutyl. Exemplary catalysts are tetra-n-butylammonium acetate (TBAA), tetra-n-butylammonium formate, tetra-n-butylammonium benzoate, tetra-n-butylammonium-2-ethylhexanoate, tetra-n-butylammonium-p-ethylbenzoate, and tetra-n-butylammonium propionate, or a combination of two or more thereof. Particularly suitable catalysts are tetra-n-butylammonium acetate and tetra-n-butylammonium formate, tetramethylammonium acetate, tetramethylammonium benzoate, tetrahexylammonium acetate, dimethylanilium formate, dimethylammonium acetate, tetramethylammonium carboxylate, tetramethylammonium-2-ethylhexanoate, benzyltrimethylammonium acetate, tetraethylammonium acetate, tetraisopropylammonium acetate, triethanol-methylammonium acetate, diethanoldimethylammonium acetate, monoethanoltrimethylammonium acetate, ethyltriphenylphosphonium acetate.

Generally, the catalyst should be added in an amount that will not affect or impair the physical properties of the coating, but in a sufficient amount to catalyze the curing reaction. In one embodiment, the catalyst is provided in an amount ranging from 1 ppm to about 75 ppm; from about 10 ppm to about 70 ppm; even from about 20 ppm to about 60 ppm. Here, as elsewhere in the specification and claims, numerical values may be combined to form new and non-disclosed ranges. The "ppm" value of the catalyst may be defined as total moles of catalyst per total weight solid of the coating.

The present silicone polymers or compositions employing such polymers may be used in a variety of compositions and applications including, but not limited to, personal care, health care, household, paints, automotive, coatings, laundry detergent, textile treatment, oil and gas, fuel cell, construction product, aerospace product, medical product, electronic application, agriculture, membranes, adhesives, sealants, injection moldable and compression moldable rubbers and plastics, and various silicone based rubbers.

A blend of the polymers with a silicone fluid may provide a physical gel suitable for use in personal care applications and composition such as, but not limited to, cosmetics, sunscreen, hair products such as shampoo or conditioner, lotions, creams, etc. Examples of personal care products include, but are not limited to, antiperspirant/deodorants, including sprays, sticks and roll-on products, shaving products, skin lotions, moisturizers, toners, bath products, cleansing products, shampoos, conditioners, combined shampoo/conditioners, mousses, styling gels, hair sprays, hair dyes, hair color products, hair bleaches, waving products, hair straighteners, nail polish, nail polish remover, nail creams and lotions, cuticle softeners, sunscreen, insect repellent, anti-aging products, lipsticks, foundations, face powders, eye liners, eye shadows, blushes, makeup, mascaras, moisturizing preparations, foundations, body and hand preparations, skin care preparations, face and neck preparations, tonics, dressings, hair grooming aids, aerosol fixatives, fragrance preparations, aftershaves, make-up preparations, soft focus applications, night and day skin care preparations, non-coloring hair preparations, tanning preparations, synthetic and non-synthetic soap bars, hand liquids, nose strips, non-woven applications for personal care, baby lotions, baby baths and shampoos, baby conditioners, shaving preparations, cucumber slices, skin pads, make-up removers, facial cleansing products, cold creams, sunscreen products, mousses, spritzes, paste masks and muds, face masks, colognes and toilet waters, hair cuticle coats, shower gels, face and body washes, personal care rinse-off products, gels, foam baths, scrubbing cleansers, astringents, nail conditioners, eye shadow sticks, powders for face or eye, lip balms, lip glosses, hair care pump sprays and other non-aerosol sprays, hair-frizz-control gels, hair leave-in conditioners, hair pomades, hair de-tangling products, hair fixatives, hair bleach products, skin lotions, pre-shaves and pre-electric shaves, anhydrous creams and lotions, oil/water, water/oil, multiple and macro and micro emulsions, water-resistant creams and lotions, anti-acne preparations, mouthwashes, massage oils, toothpastes, clear gels and sticks, ointment bases, topical wound-healing products, aerosol talcs, barrier sprays, vitamin and anti-aging preparations, herbal-extract preparations, bath salts, bath and body milks, hair styling aids, hair-, eye-, nail- and skin-soft solid applications, controlled-release personal care products, hair conditioning mists, skin care moisturizing mists, skin wipes, pore skin wipes, pore cleaners, blemish reducers, skin exfoliators, skin desquamation enhancers, skin towelettes and cloths, depilatory preparations, personal care lubricants, nail coloring preparations, sunscreens, cosmetics, hair care products, skin care products, toothpastes, drug delivery systems for topical application of medicinal compositions that are to be applied to the skin and combinations comprises at least one of the foregoing applications Personal care compositions can include various ingredients such as a carrier, pigment, film formers, emulsifiers, vitamins, plasticizers, surfactants, antioxidants, waxes, oils, solvents, etc.

In one embodiment, a personal care product may optionally contain 0-90 parts by weight pigments. Pigments suitable for use herein are all inorganic and organic colors/pigments. These are usually aluminum, barium or calcium salts or lakes. Lakes are either a pigment that is extended or reduced with a solid diluent or an organic pigment that is prepared by the precipitation of a water-soluble dye on an adsorptive surface, which usually is aluminum hydrate. A lake also forms from precipitation of an insoluble salt from an acid or basic dye. Calcium and barium lakes are also used herein. Suitable lakes include, but are not limited to, Red 3 Aluminum Lake, Red 21 Aluminum Lake, Red 27 Aluminum Lake, Red 28 Aluminum Lake, Red 33 Aluminum Lake, Yellow 5 Aluminum Lake, Yellow 6 Aluminum Lake, Yellow 10 Aluminum Lake, Orange 5 Aluminum Lake and Blue 1 Aluminum Lake, Red 6 Barium Lake, Red 7 Calcium Lake. Other colors and pigments can also be included in the compositions, such as pearls, titanium oxides, Red 6, Red 21, Blue 1, Orange 5, and Green 5 dyes, chalk, talc, iron oxides and titanated micas.

A personal care composition may optionally contain 0-99 parts by weight organic film former known in the prior arts. The film-forming agent may be any which is cosmetically acceptable. Examples of useful film-forming agents include natural waxes, polymers such as polyethylene polymers, and copolymers of PVP, ethylene vinyl acetate, dimethicone gum, and resins, such as shellac, polyterpenes.

A personal care composition may optionally include 0-50 parts by weight either blocking or absorbing sunscreening agents. Blocking sunscreening agents are generally inorganic, such as various cesium oxides, chromium oxides, cobalt oxides, iron oxides, red petrolatum, silicone- and other treated titanium dioxides, titanium dioxide, zinc oxide, and/or zirconium oxide, $BaTiO_3$, $CaTiO_3$, $SrTiO_3$ and SiC. Absorbing sunscreening agents, which are usually organic species, are particularly useful. Such absorbing sunscreening agents include, but are not limited to, UV-A absorbers, which generally absorb radiation in the 320 to 400 nm region of the ultraviolet spectrum, for example anthranilates, benzophenones, and dibenzoyl methanes; and UV-B absorbers, which generally absorb radiation in the 280 to 320 nm region of the ultraviolet spectrum, for example, p-aminobenzoic acid derivatives, camphor derivatives, cinnamates, and salicylates. Specific examples of organic sunscreening agents include p-aminobenzoic acid, avobenzone cinoxate, dioxybenzone, homosalate, menthyl anthranilate, octocrylene, octyl methoxycinnamate, octyl salicylate, oxybenzone, padimate, phenylbenzimidazole sulfonic acids, sulisobenzone, trolamine salicylate, aminobenzoic acid, amyldimethyl p-aminobenzoic acid, diethanolamine p-methoxycinnamate, digalloyl trioleate, 2-ethylhexyl-2-cyano-3,3-diphenylacrylate, ethylhexylp-methoxycinnamate, 2-ethylhexyl salicylate, glyceryl aminobenzoate, homomenthyl salicylate, homosalate, 3-imidazol-4-ylacrylic acid and the ethyl ester thereof, methyl anthranilate, octyldimethyl PABA, 2-phenylbenzimidazole-5-sulfonic acid and salts, sulisobenzone, triethanolamine salicylate, N,N,N-trimethyl-4-(2-oxoborn-3-ylidene methyl)anillinium methyl sulfate, aminobenzoate, 4-isopropylbenzyl salicylate, 2-ethylhexyl 4-methoxycinnamate, methyl diisopropylcinnamate, isoamyl 4-methoxycinnamate, diethanolamine 4-methoxycinnamate, 3-(4'-trimethylammonium)-benzyliden-boman-2-one methylsulfate, 2-hydroxy-4-methoxybenzophenone, 2-hydroxy-4-methoxybenzophenone-5-sulfonate, 2,4-dihydroxybenzophenone, 2,2',4,4'-tetrahydroxybenzophenone, 2,2'-dihydroxy-4,4'dimethoxybenzophenone, 2-hydroxy-4-n-octoxybenzophenone, 2-hydroxy-4-methoxy-4'-methoxybenzophenone, ca-(2-oxoborn-3-ylidene)-tolyl-4-sulfonic acid and soluble salts thereof, 3-(4'-sulfo)benzyliden-bornan-2-one and soluble salts thereof, 3-(4'-methylbenzylidene)-d,l-camphor, 3-benzylidene-d,l-camphor, benzene 1,4-di(3-methylidene-10-camphosulfonic) acid and salts thereof, urocanic acid, 2,4,6-tris-(2'-ethylhexyl-1'-oxycarbonyl)-anilinol 1,3,5-triazine, 2-(p-(tert-butylamido)anilinol-4, 6-bis-(p-(2'-ethylhexyl 1'-oxycarbonyl) anilinol 1,3,5-triazine, 2,4-bis{1,4-(2-ethylhexyloxy)-2-hydroxyl-phenyl}-6-(4-methoxyphenyl)-1,3,5-triazine, the polymer of N-(2 et 4)-(2-oxoborn-3-yliden)methylbenzyl acrylamide, 1,4-bis-benzimidazolyl-phenylen-3,3',5,5'-tetrasulfonic acid and salts thereof, the benzalmalonate-substituted polyorganosiloxanes, the benzotriazole-substituted polyorganosiloxanes (Drometrizole Trisiloxane), solubilized 2,2'-methylene-bis-1,6-(2H-benzotriazol-2-yl)-4-(1,1,3,3-tetramethylbutyl) phenol, 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-dimethoxydibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4-tert-butyl-4'-methoxydibenzoylmethane, and combinations comprising at least one of the foregoing sunscreening agents.

A personal care composition can be specifically formulated for use as, but not limited to, a color cosmetic, sunscreen, hair conditioner, a moisturizer, etc. Suitable forms and formulations for such application are known to those of ordinary skill in the art. For example, when formulated for use as a sunscreen, the composition may be in the form of a lamellar emulsion, a mirocoemulsion, or a nanoemulsion. In addition, the emulsions may be a fluid simple emulsion, a fluid multiple emulsion, a rigid simple emulsion, or a rigid multiple emulsion. The simple emulsion or multiple emulsion may comprise a continuous aqueous phase containing dispersed lipid vesicles or oil droplets, or a continuous fatty phase dispersed lipid vesicles or water droplets. In one embodiment, the sunscreen application is an emulsion having a continuous aqueous phase, and may be in the form of a stick, a lotion, a gel, a spray, and the like. Suitable emulsifiers for the formation of sunscreen emulsions include, for example ethoxylated surfactants known in the art such as Polysorbate-20, Laureth-7, Laureth-4, Sepigel® 305 available from SEPPIC, oils such as vegetable and mineral oil; animal and/or synthetic waxes such as beeswax, paraffin, rice bran wax, candelilla wax, carnauba wax and derivatives thereof; and hydrocarbon gels or bentone type gels, such as Gel SS71, Gel EA2786, Quaternium-18 Bentonite, 38 CE, Gel ISD V or Gel ISD; and organosilicone emulsifiers such as cetyl dimethicone copolyol-polyglyceryl4-isostearate-hexylaurate (ABIL® WE 09) available from Goldschmidt Chemical Corporation, behenate dimethicone, cetyl dimethicone copolyol (ABIL® EM 90), (ABIL® EM 97), laurylmethicone copolyol (5200), cyclomethicone and dimethicone copolyol (DC 5225 C and DC 3225 C), cyclopentasiloxane and dimethicone copolyol (SF 1528).

A personal care composition may optionally contain vitamins or skin nourishing agents. Some suitable agents are ceramides, hyaluronic Acid, panthenol, peptides (copper hexapeptide-3), AHA's (lactic acid), retinols (retinyl palmitate)-Vit. A derivatives, vitamin C (1-ascorbic acid), BHA's (salicylic Acid), teas (Green Tea, White Tea, Red Tea), soy and other plant derivatives, isoflavones (Grape Seed Extract), argireline, acai berry.

Plasticizers may also be added to the formulation to improve the flexibility and cosmetic properties of the resulting formulation. Plasticizers are frequently used to avoid brittleness and cracking of film formers, and include, for example, lecithin, polysorbates, dimethicone copolyol, glycols, citrate esters, glycerin, and dimethicone. One skilled in the art may routinely vary the amount of plasticizer desired based on the properties desired and the application envisaged.

The polymers of the present invention can be incorporated into a carrier, such as a volatile carrier which quickly volatilizes after application. The volatile carriers can be selected from volatile hydrocarbons, volatile silicones, and mixtures thereof.

Hydrocarbon oils useful in personal care products include those having boiling points in the range of 60-260° C., including hydrocarbon oils having from about $C_8$ to about $C_{20}$ chain lengths, even $C_8$ to $C_{20}$ isoparaffins. Examples include isododecane, isohexadecane, isoeocosane, 2,2,4-trimethylpentane, 2,3-dimethylhexane, and mixtures of two or more thereof.

Suitable volatile silicone fluids include cyclomethicones having 3, 4 and 5 membered ring structures corresponding to the formula $(R_2SiO)_x$, where x is from about 3 to about 6.

What has been described above includes examples of the present specification. It is, of course, not possible to describe every conceivable combination of components or methodologies for purposes of describing the present specification, but one of ordinary skill in the art may recognize that many further combinations and permutations of the present specification are possible. Accordingly, the present specification is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

EXAMPLES

Example 1: Diphenyl Sulfone Functionalized Polyorganosiloxane Bearing Terminal Allyoxy Ether Group To a solution of Allyloxy diphenyl sulfone (16.9 g, 0.051 mol) & Karstedt's catalyst (5 ppm of 2 wt % Pt) in toluene (100 mL) in a three neck round bottom flask fitted with a reflux condenser, dropping funnel, and a mechanical stirrer under nitrogen environment, polydimethylsiloxane bearing terminal hydride group (Hyd eqv. 0.952) (334.52 g, 0.151 mol) was added dropwise over a period of 30 min. The reaction temperature increased to 85° C. and allowed to continue till all the hydride peak get disappeared from the $^1$H-NMR. The resulting allyloxy ether terminated polymer was vacuum stripped at 150 degree Celsius for 3 h to remove the volatile compounds and the solvent. The product was obtained as a high viscous liquid. (GPC: $M_n$=12392, PDI-1.8; Vis: 6 Pa·S).

Example 2: Diphenyl Sulfone Functionalized Polyorganosiloxane Bearing Terminal Hydride Groups To a solution of Allyloxy diphenyl sulfone (25 g, 0.076 mol) & Karstedt's catalyst (0.09 g, 5 ppm of 2 wt % Pt) in Toluene (150 mL) at 75° C., polydimethylsiloxane bearing terminal hydride group (Hyd eqv. 0.952) (334.52 g, 0.151 mol) was added dropwise over a period of 30 min. The reaction temperature was subsequently increased to 85° C. and allowed to continue till all the allylic peak disappeared from the $^1$H-NMR. The resulting hydride terminated polymer was vacuum stripped at 150 degree Celsius for 3 h to remove the volatile compounds and the solvent. The product was obtained as a low viscous liquid. (GPC: $M_n$=3069 g/mol, PDI-1.7; Vis: 0.33 Pa·S).

Example 3: Diphenyl Sulfone Functionalized Polyorganosiloxane Bearing Terminal Vinyl Groups To a reaction mixture of hydride terminated diphenyl sulfone functionalized polyorganosiloxane (71.9 g) (obtained in the example 2), toluene (30 mL), and platinum catalyst (5 ppm of 2% Pt) was added 1,3-Divinyltetramethyldisiloxane (8.88 g, 0.048 mol) and refluxed at 110 degree Celsius. The reaction was continued till all the hydride signals get disappeared from the $^1$H-NMR. The resulting polymer was finally vacuum stripped at 150 degree Celsius for 3 h to remove the volatile compounds and the solvent. The final product was obtained as a low viscous liquid. (GPC: Mn=5014 g/mol, PDI-1.9; Vis: 0.56 Pa·S).

Example 4: Diphenyl Sulfone Functionalized Polyorganosiloxane Bearing Terminal Epoxy Ether Groups To a reaction mixture of hydride terminated diphenyl sulfone functionalized polyorganosiloxane (43.1 g) (obtained in the example 2), toluene (20 mL), and platinum catalyst (5 ppm of 2% Pt) was added allylglycidyl ether (2.72 g, 0.024 mol) and continued to reflux at 75 degree Celsius till all the hydride gets capped by the epoxy ether. The polymer was recovered by vacuum stripping the reaction mixture at 90 degree Celsius for 4 h. The product was obtained as a low viscous liquid. (GPC: Mn=4073 g/mol, PDI-1.6; Vis: 0.41 Pa·S).

Example 5: Diphenyl Sulfone Functionalized Polyorganosiloxane Bearing Terminal Epoxy Groups To a reaction mixture of hydride terminated diphenyl sulfone functionalized polyorganosiloxane (185.5 g) (obtained in the example 2), toluene (80 mL), and platinum catalyst (5 ppm of 2% Pt) was added 1,2-epoxy-4-vinylcyclohexene (12.71 g, 0.102 mol) and continued to reflux at 75 degree Celsius till all the hydride gets capped by the vinyl cyclohexyl epoxide. The polymer was recovered by vacuum stripping the reaction mixture at 90 degree Celsius for 4 h. The product was obtained as a low viscous liquid. (GPC: Mn=3992 g/mol, PDI-1.7; Vis: 0.47 Pa·S)

Example 6: Diphenyl Sulfone Functionalized Polyorganosiloxane Bearing Terminal Methacrylate Groups To a reaction mixture of hydride terminated diphenyl sulfone functionalized polyorganosiloxane (86.3 g) (obtained in the example 2), toluene (40 mL), Hydroquinone monomethyl ether (300 ppm) and platinum catalyst (5 ppm of 2% Pt) was added allyl methacrylate (6.01 g, 0.048 mol) and continued the reaction at 75 degree Celsius till all the hydride gets capped by the methacrylate functional group. The polymer was recovered by vacuum stripping the reaction mixture at 110 degree Celsius for 5 h. The product was obtained as a low viscous liquid. (GPC: Mn=5754 g/mol, PDI-1.9; Vis: 0.53 Pa·S)

Example 7: Diphenyl Sulfone Functionalized Polyorganosiloxane Bearing Terminal Trimethoxysilyl Groups To a reaction mixture of hydride terminated diphenyl sulfone functionalized polyorganosiloxane (50.3 g) (obtained in the example 3), toluene (20 mL), and platinum catalyst (5 ppm of 2% Pt) was added vinyltrimethoxysilane (4.9 g, 0.033 mol) and continued the reaction at 110 degree Celsius till all the hydride gets capped by the trimethoxy silane. The polymer was recovered by vacuum stripping the reaction mixture at 150 degree Celsius for 3 h. The product was obtained as a low viscous liquid. (GPC: Mn=3431 g/mol, PDI-1.9; Vis: 0.41 Pa·S)

While the above description contains many specifics, these specifics should not be construed as limitations on the scope of the invention, but merely as exemplifications of preferred embodiments thereof. Those skilled in the art may envision many other possible variations that are within the scope and spirit of the invention as defined by the claims appended hereto.

What is claimed is:

1. A polymer of the formula:

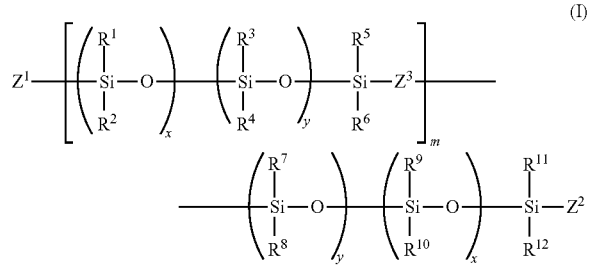
(I)

where $R^1$-$R^{12}$ are independently chosen from a hydrogen, a C1-C10 monovalent hydrocarbon group optionally containing a hetero atom, a C6-C20 monovalent aromatic group, and a C4 to C30 monovalent saturated or unsaturated cycloalkyl group optionally containing a hetero atom, siloxy group containing 1-20 silicon atoms, —OH, —NH2, or —COOH;

$Z^1$ and $Z^2$ are independently chosen from a C1-C10 hydrocarbon group optionally containing heteroatom, —OH, —NH2, —COOH, or $R^{16}$-A-$R^{17}$— where A is chosen from a group comprising of a unsaturated cyclic group chosen from an aromatic group, a functionalized aromatic group, a fused aromatic group optionally containing a heteroatom, a unsaturated alicyclic group, a unsaturated heterocyclic group, or a combination of two or more thereof; $R^{16}$ and $R^{17}$ are independently chosen from a nil, C1-C10 hydrocarbon group, a C6-C20 aromatic group and a C4 to C30 saturated or unsaturated cycloalkyl group, wherein when one of $Z^1$ or $Z^2$ is $R^{16}$-A-$R^{17}$- then both $Z^1$ and $Z^2$ will not be $R^{16}$-A-$R^{17}$—;

$Z^3$ is chosen from —$R^{19}$-A-$R^{19}$— where A is chosen from

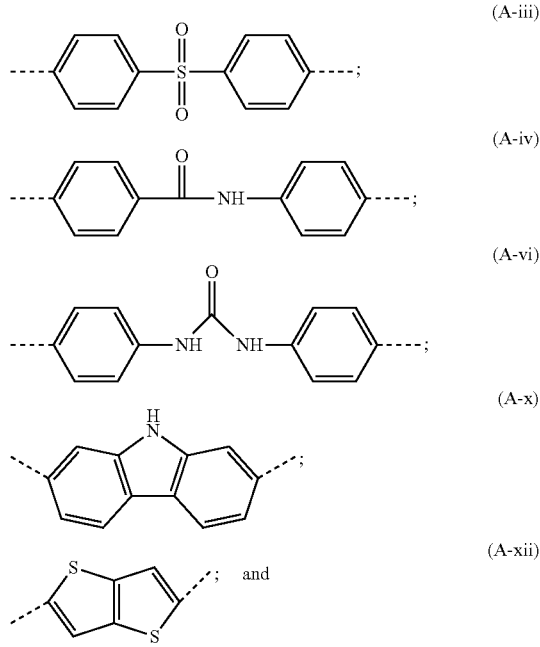

(A-iii)
(A-iv)
(A-vi)
(A-x)
(A-xii)
and

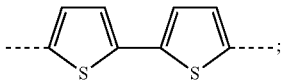
(A-xiii)

and $R^{19}$ is chosen from a C2-C10 hydrocarbon group, a C6-C20 aromatic group, and a C4 to C30 saturated or unsaturated cycloalkyl group; and m is 1-100; x is 0-200; and y is 0-200, wherein x+y≥1; wherein the polymer is thermally conductive.

2. The polymer of claim 1, wherein A in $Z^1$ and $Z^2$ is independently chosen from a C6 to C12 aromatic group; a C10-C36 fused aromatic ring group; a C4-C36 unsaturated alicyclic group; and a C4-C36 unsaturated heterocyclic group.

3. The polymer of claim 1, wherein A in one or more of $Z^1$ or $Z^2$, is chosen from a group of the formula -$A^1$-$R^{18}$-$A^2$- where $A^1$ and $A^2$ are independently chosen from a C6 to C12 aryl group, C12-C36 fused aromatic ring group, a C5-C36 unsaturated alicyclic group, and a C5-C36 unsaturated heterocyclic group; and $R^{18}$ is chosen from a direct bond —$(CH_2)_n$—, —$C(CH_3)_2$—, —O—, —S—, —$S(O)_2$—, —C(O)—, C(O)—NH—, —NH—C(O)—NH—, C(O)—O—, —CH=N—, or —CH=N—N=CH— where n is 1-10.

4. The polymer of claim 1, wherein A in $Z^1$, $Z^2$, and $Z^3$ is

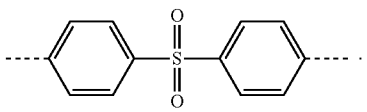

5. The polymer of claim 1 having a number average molecular weight of from about 1000 g/mol to about 50000 g/mol.

6. An automotive product, household product, paint, coating, laundry detergent, textile treatment, oil or gas product, fuel cell, electronic product, agriculture product, aerospace product, medical or health care product, membrane, construction product, adhesive, sealant, injection moldable and compression moldable rubber or plastic, or silicone based rubber, comprising the polymer of claim 1.

7. The products of claim 6 selected from a light emitting device, a computer device, a stacked die, a mobile phone, a tablet, a flip chip package, a hybrid memory cube, a touch screens, a Wi-Fi device, an automotive technology hifi systems, a through-silicon via device, an audio system, a heat pipe, a water tank, a fuel cell, a wind turbine, a computer chip, a gaming console, a data transfer device, a light device, a battery, a housing, a cooler, a heat exchanging device, a wire, a cable, a heating wire, a refrigerator, a dishwasher, an air conditioning device, an accumulator, a transformer, a laser, functional clothing, a car seat, a medical device, a fire protection device, an electric motor, a plane, a train, a filament for 3D printing material, a drug delivery systems, a transdermal patch, a wound healing patches, a wound dressing patch, a patche for scar reduction, a transdermal iontophoresis, a scaffold for tissue engineering, an anti-microbial device, a wound management device, an ophthalmic device, a bioinsert, a prosthese, a body implant, a paint, a structural coating, a masonry coating, a marine coating, a seed coating, a superspreader or a controlled release fertilizer.

8. A personal care product comprising the polymer of claim 1.

9. The personal care product of claim 8 in the form of an antiperspirant/deodorant, a shaving product, a skin lotion, a moisturizer, a toner, a bath product, a cleansing product, a shampoo, a conditioner, a combined shampoo/conditioners, a mousse, a styling gel, a hair spray, a hair dye, a hair color product, a hair bleach, a waving products, a hair straightener, a nail polish, a nail polish remover, a nail cream or lotions, a cuticle softener, a sunscreen, an insect repellent, an anti-aging product, a lipstick, a foundation, a face powder, an eye liner, an eye shadow, a blush, a makeup, a mascara, a moisturizing preparation, a foundation, a body and hand preparation, a skin care preparation, a face and neck preparation, a tonic, a dressing, a hair grooming aid, an aerosol fixative, a fragrance preparation, an aftershave, a make-up preparation, a soft focus application, a night and day skin care preparation, a non-coloring hair preparation, a tanning preparation, a synthetic and non-synthetic soap bar, a hand liquid, a nose strip, a non-woven application for personal care, a baby lotion, a baby shampoo, a baby conditioner, a shaving preparation, a cucumber slices, a skin pads, a make-up remover, a facial cleansing product, a cold cream, a sunscreen product, a spritzer, a paste mask and mud, a face mask, a cologne and toilet water, a hair cuticle coat, a shower gel, a face and body wash, a personal care rinse-off products, a gel, a foam bath, a scrubbing cleanser, an astringent, a nail conditioner, an eye shadow stick, a powder for face or eye, a lip balm, a lip gloss, a hair care pump spray, a hair-frizz-control gel, a hair leave-in conditioner, a hair pomade, a hair de-tangling product, a hair fixative, a hair bleach product, a skin lotion, a pre-shave and pre-electric shave, an anhydrous cream and lotion, an oil/water emulsion, a water/oil emulsion, a water-resistant cream or lotion, an anti-acne preparation, a mouth-wash, a massage oil, a toothpaste, a clear gel or stick, an ointment base, a topical wound-healing product, an aerosol talc, a barrier spray, a vitamin and anti-aging preparation, an herbal-extract preparation, a bath salt, a bath and body milk, a hair styling aid, a hair-, eye-, nail- and skin-soft solid application, a controlled-release personal care product, a hair conditioning mist, a skin care moisturizing mist, a skin wipe, a pore skin wipe, a pore cleaner, a blemish reducer, a skin exfoliator, a skin desquamation enhancer, a skin towelette or cloth, a depilatory preparation, or a personal care lubricant.

\* \* \* \* \*